United States Patent [19]

Benin

[11] Patent Number: 4,476,631
[45] Date of Patent: Oct. 16, 1984

[54] CUTTING MEANS MAGAZINE FOR A STERILE DOCKING APPARATUS

[75] Inventor: Joshua Benin, Newark, Del.

[73] Assignee: E. I. Du Pont de Nemours and Company, Wilmington, Del.

[21] Appl. No.: 408,415

[22] Filed: Aug. 16, 1982

[51] Int. Cl.$^3$ .............................................. B23D 21/00
[52] U.S. Cl. .......................................... 30/92; 30/40.2
[58] Field of Search ........................... 30/40.2, 40, 92; 604/29; 206/349, 354; 221/232

[56] References Cited

U.S. PATENT DOCUMENTS

| | | | |
|---|---|---|---|
| 1,730,167 | 10/1929 | Schick . | |
| 1,737,696 | 12/1929 | Allen . | |
| 2,200,752 | 5/1940 | Kuhnl | 30/40.2 X |
| 2,215,008 | 9/1940 | Kuhnl | 30/40.2 X |
| 2,436,025 | 2/1948 | Steinbach | 221/232 |
| 2,676,396 | 4/1954 | Testi | 30/40 |
| 2,680,291 | 6/1954 | Shnitzler et al. | 30/40 |
| 2,686,967 | 8/1954 | Landwehr | 30/40 |
| 2,697,276 | 12/1954 | Austin | 30/40 |
| 2,718,963 | 9/1955 | Austin . | |
| 2,812,576 | 11/1957 | Kuhnl | 30/40 |
| 2,874,461 | 2/1959 | Austin | 30/40 |
| 3,180,484 | 4/1965 | Kuhnl | 30/40.2 X |
| 3,850,343 | 11/1974 | Petrillo | 30/40 X |
| 4,369,779 | 1/1983 | Spencer | 604/29 |

Primary Examiner—Jimmy C. Peters

[57] ABSTRACT

There is disclosed a cutting means magazine for a sterile docking device for forming a connection between two thermoplastic tubes comprising a casing, a stack of disposable cutting means therein, and spring means urging the stack against a wall of the casing. The casing has an exit slot for ejection of the uppermost cutting means and a slot for an ejector, the latter slot having upstream and downstream access openings. The upstream access opening (a) has an ejector aligning surface with a rise of at least about 0.25 mm and a slope of up to 45° and (b) being from about 50%–100% of the cutting means thickness. The downstream access opening is from about 10%–80% greater than the cutting means thickness.

13 Claims, 4 Drawing Figures

CUTTING MEANS MAGAZINE FOR A STERILE DOCKING APPARATUS

BACKGROUND OF THE INVENTION

This invention relates to a magazine for holding a stack of cutting means elements. More specifically, the present invention relates to a cutting means magazine for use in an apparatus for forming a sterile connection (sterile docking) between two tubes.

U.S. patent application Ser. No. 267,291, filed on June 4, 1981 now U.S. Pat. No. 4,369,779, discloses an apparatus for forming a sterile connection comprising a cutting means, means adapted to heat said cutting means, a pair of mounting blocks adapted to receive and hold two tubes to be joined, means to provide movement between said blocks and said cutting means to a position such that the cutting means is between said blocks and traversing where the blocks are adapted to receive tubes, means adapted to realign said blocks to a position where two different tube ends are aligned with and facing each other, and means to separate said blocks and said cutting means while urging said blocks together. The application discloses that the cutting means can take many forms, can have the shape of a knife, can be either permanent or disposable, and can be a composite made according to printed circuit technology in single blades or blades mounted in a magazine.

During the further development of the aforesaid sterile docking device having incorporated therein a cutting means magazine it was found that during feeding occasionally two cutting means were fed instead of one causing jamming in the exit slot and that sometimes the feeder arm or ejector would miss or lose its grip on the cutting means resulting in no cutting means being advanced into the cutting means holder. In the first situation, no cutting means is advanced even though the ejection arm completes its forward stroke and indicates a fresh cutting means is in proper position. Thus, the next sterile docking operation would then be tried with an old cutting means. In the second situation, a fresh cutting means may be advanced only part way even though the ejection arm completes its forward stroke and indicates that a fresh cutting means is in proper position. If a sterile docking operation were attempted with the apparatus in this situation, the docking mechanism would jam on the partially advanced cutting means. Thus, there exists a need for an improved cutting means magazine which would minimize the foregoing problems.

Various blade magazines have been disclosed in the art. U.S. Pat. No. 1,737,696 issued to Allen on Dec. 3, 1929 discloses a blade holding magazine to be used in combination with a razor blade, said magazine comprising a rectangular chamber in which blades are held, a cover closing the chamber, a spring to press the blades toward the cover, and a push bar or blade feeding member slidably mounted in the magazine directly under the cover and capable of being reciprocated to discharge blades from the magazine. U.S. Pat. No. 2,676,396 issued to Testi on Apr. 27, 1954 discloses a combination of a safety razor and a blade magazine. The magazine includes in its structure an elongated rectangular shell having a bottom, sides and top flanges which extend inwardly toward each other but are separated by a substantially open space. One end of the magazine is open for reception of the razor head and the other end has a rear wall formed by a base plate. The magazine is provided with a feed slide having side flanges which engage the walls of the shell and an inner blade engaging plate which is connected to the slide by a stud. A bowed spring is used to maintain the stack of blades in contact with the top flanges.

U.S. Pat. No. 2,680,291 issued to Shnitzler et al. on June 8, 1954 discloses a blade magazine comprising an elongated channel shaped plastic casing with parallel side walls having opposed grooves and end walls, one of the end walls being recessed at an upper corner, one side wall having an open cut-away portion at its end opposite to the recessed end wall, and a sheet metal cover fitting at its edges in said grooves and having at one end an ear bent into the recess of said end wall and at the other end an angular section bent into the open cut-away portion in the side wall of the casing, thus positively holding the cover against longitudinal displacement in either direction on the casing. The magazine has a bowed spring for holding the uppermost blade in contact with the inner face of the cover and the front end wall of the casing terminates slightly below the opposed grooves in the side walls of the casing and thus defines an exit slit at the end of the magazine. A feed slide is mounted to the cover of the magazine.

U.S. Pat. No. 2,718,963 issued to Austin on Sept. 27, 1955 discloses a razor blade magazine comprising a casing, a stack of single edged blades therein and a spring urging the stack against a wall of the casing, the casing having an exit slot aligned with the top blade of the stack to permit ejection thereof and a pusher slot for accommodating a blade ejector, the pusher slot extending diagonally across the top blade of the stack from a point adjacent a back corner of the blade near the exit slot to a point adjacent an edge corner of the blade near the opposite end of the casing. The blade ejector is external to the magazine.

Other patents which disclose blade magazines include U.S. Pat. No. 3,850,343 which specifies that the thickness of the blade pusher web is less than the thickness of a blade unit and U.S. Pat. Nos. 2,686,967, 2,697,276 and 2,812,576.

SUMMARY OF THE INVENTION

The present invention provides a cutting means magazine for use in an apparatus for forming a connection between two thermoplastic tubes comprising a casing, a stack of disposable cutting means therein, and spring means urging the stack against a wall of the casing; said casing having an exit slot for ejection of the uppermost cutting means of the stack and a cutting means ejection slot for accommodating an ejector said slot being centrally located in the wall against which the stack is urged and having an upstream access opening to the cutting means and a downstream cutting means access opening which has the exit slot as part thereof; the upstream access opening (A) having an ejector aligning surface with a rise of at least about 0.25 mm (0.010 inch) and a slope of up to 45° and (B) being from about 50% to about 100% of the cutting means thickness; the downstream access opening being from about 10% to about 80% greater than the cutting means thickness. The present invention minimizes the occurrences of failures to feed and partial feeding of cutting means.

DETAILED DESCRIPTION OF THE INVENTION

The cutting means magazine of the invention is for use with a sterile docking device in accordance with copending U.S. patent application Ser. No. 267,291, now U.S. Pat. No. 4,369,779, the pertinent parts of which are incorporated herein by reference, and is preferably used with the automatic sterile docking device described and claimed in copending U.S. patent application Ser. No. 408,418, filed concurrently herewith.

Figure 1:
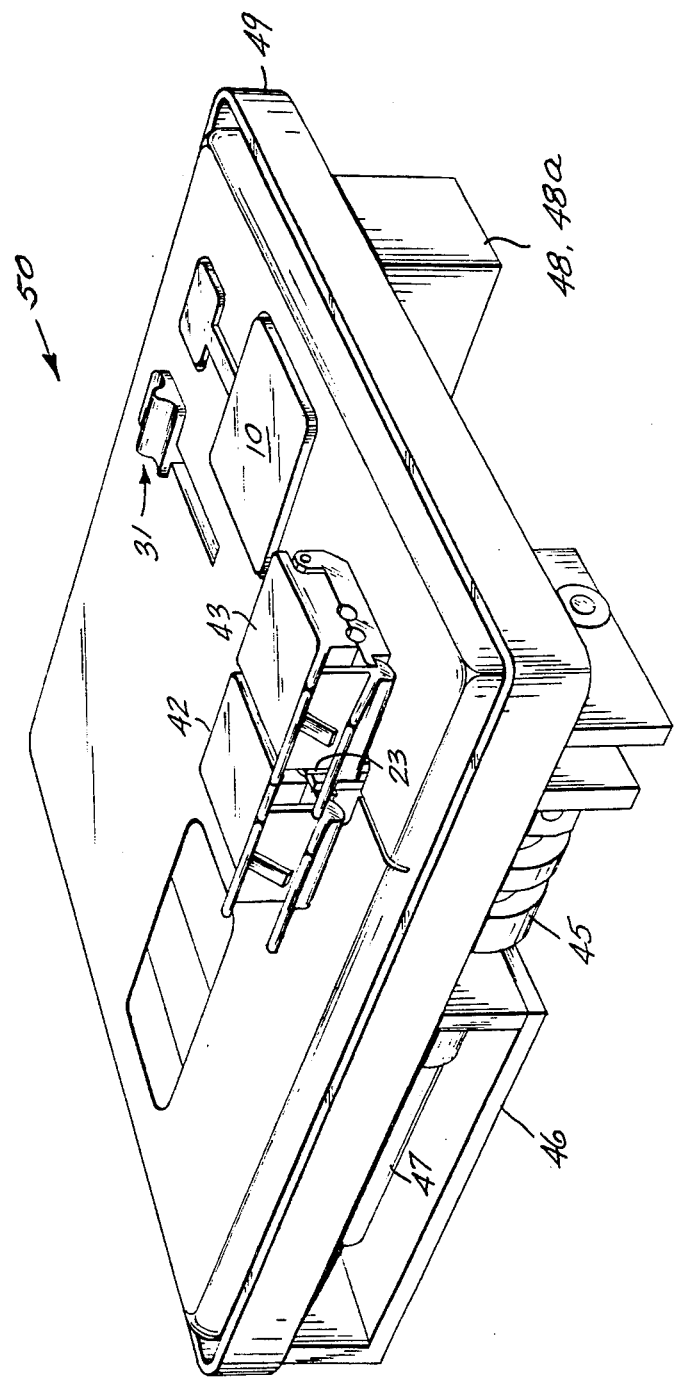
FIG. 1 is an isometric view of an automatic splicing (sterile connection) device with which the magazine is used.

Referring to FIG. 1, magazine 10 of the invention is shown in arrangement in the aforesaid automatic sterile docking device. The device is denoted generally by 50 and includes as major components a frame 49, a cutting means 23 pivotally connected to the frame, a pair of mounting blocks 42 and 43 spaced from each other in the same plane, an evacuation pump 48a driven by a motor 48, a cam cylinder 45 driven by a motor 47 and an electronic control unit 46. Knob 31 provides for operation of the ejection system for the magazine.

Figure 2:
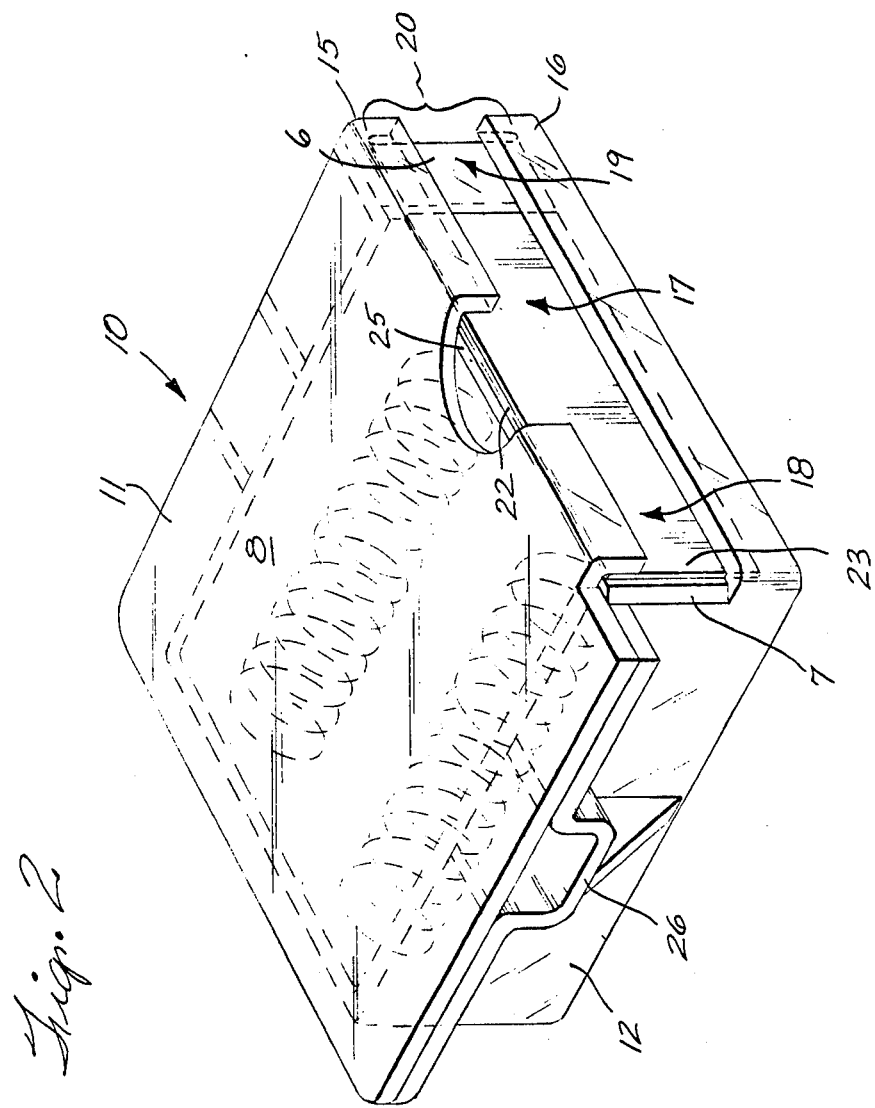
FIG. 2 is a perspective view of the cutting means magazine of the invention.

Referring to FIG. 2, the magazine chosen for purposes of illustration is denoted as 10 and includes a generally rectangular housing 8 defined by a lower wall or bottom 9 (not shown), an upper wall 11, side walls 12 and 13 (wall 13 is not shown), a rear wall 14 (not shown) extending between the side walls, and a pair of longitudinally extending flange portions 15 and 16. Walls not shown in FIG. 2 can be seen in FIG. 4. Housing 8 is rigid and can be made from any suitable material and, for the embodiment shown in FIG. 2, is made from a plastic material. Contained in housing 8 is a stack 22 of cutting means 23, a plate 25 beneath the lowermost cutting means and spring means (not shown).

Flange portion 15 extends inwardly from upper wall 11 and flange portion 16 extends inwardly from lower wall 9. The inner edges of flange portions 15 and 16 are spaced apart to define a slot 17 which extends beyond side wall 13 and provides for longitudinal passage of an ejector. The terms upper, lower, rear, and right are relative and refer herein to the orientation illustrated in the drawings.

Inner surfaces of the flange portions define with the right edge of side wall 12 an upstream access opening 18 permitting contact to be made by an ejector (not shown) with the edge of the uppermost blade of stack 22. The distance between the inner surfaces of flange portions and the right edge of side wall 12 is from about 50% to about 100%, preferably 75% to about 100%, of the thickness of the cutting means. In the embodiment illustrated, this distance is from 0.25 mm (0.010 inch) to 0.30 mm (0.012 inch). The height of the upstream access opening as defined by the right edge of side wall 12 and inner surfaces of the flange portions is important. The height as prescribed herein assures that the ejector will strike the edge of only one cutting means when pushed.

The right edge of side wall 12 is chamfered on its outside to provide ejection aligning surface 7 which has a rise, i.e., the perpendicular height of the bevel, of at least 0.25 mm (0.01 inch) and a slope of up to 45°, preferably up to 30°. In the embodiment illustrated the rise is about 0.64 mm (0.025 inch) and a slope of about 30°. The chamfered edge of side wall 12 operates such that, if tolerance between the ejector means position and the magazine position allows the ejector to strike the edge of side wall 12 instead of passing over it, the ejector will move to the right on the bevelled edge, by movement of the ejector or magazine, until it passes through the upstream access opening. In the sterile docking device, rear wall 14 of the magazine presses against a spring-loaded clip (not shown) attached to an ejection means and cutting means holding system, thereby enabling sufficient movement of the magazine to provide for functioning of the ejector aligning surface.

Access opening 19 which is defined by inner surfaces of flange portions 15 and 16 and the right surface of sidewall 13 has a height, defined by inner surfaces of flange portions 15 and 16 and the right surface of sidewall 13, which is from about 10% to about 80% greater than the thickness of cutting means. Exit slot 20 is also defined by the inner surfaces of flange portions 15 and 16 and the right surface of side wall 13 but extends beyond the ejector slot 17 on each side of it. Preferably, the magazine has a lip 6 which extends from the upper surface of side wall 13, thereby providing stability to the blade position as it exits the magazine and enters the blade holder.

For the specific embodiment illustrated in FIG. 2 the stack of cutting means contains about 40 cutting means each 12.7 mm (0.50 inch) wide × 34.3 mm (1.35 inch) long × 0.30 mm (0.012 inch) thick. The cutting means can be made of a variety of materials but preferably is a laminate as described in copending U.S. patent application Ser. No. 408,417, filed concurrently herewith.

Figure 3:
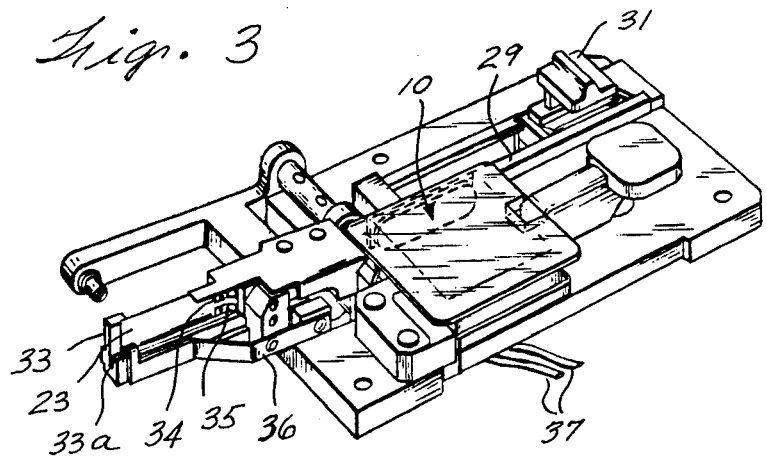
FIG. 3 is an isometric view of the cutting means magazine and the cutting means holder and ejection means with which the magazine is designed to be used.

Referring now to FIG. 3, magazine 10 is temporarily held fixedly in the ejection means and cutting means holder system of a sterile docking device. Projections 26 (FIG. 2) on the side walls provide surfaces for retaining the magazine in its proper location. A cutting means 23 is positioned in the holder 33 and retained rigidly there by clamp 36 and track 33a in the blade holder. A pair of spring loaded electrical contacts 34 and 35 joined by leads 37 to a control system (not shown) are making contact with the cutting means 23. The ejection means has pusher 31 for effecting reciprocating motion of ejector 29.

Figure 4:
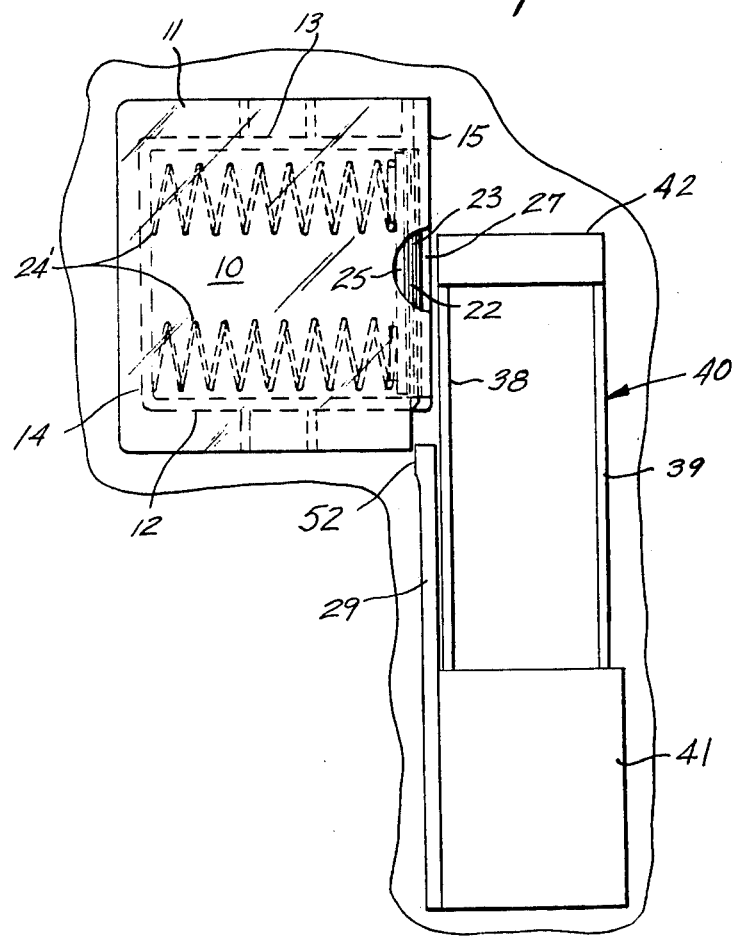
FIG. 4 is a plan view of the cutting means magazine and the ejection means.

Referring now to FIG. 4, magazine 10 is shown positioned in relation to ejector means 40 having an ejector 29 which moves on tracks 38 and 39. Ejector 29 preferably is recessed slightly near its end which makes contact with the cutting means to provide an end portion 52 which extends out from the ejector surface adjacent the uppermost cutting means. This feature enables the end portion, after it has cleared side wall 12, to press down on the stack to make better contact with the edge of the uppermost cutting means and eliminates dragging of the ejector along the right surface of side wall 12 and the surface of the next cutting means in stack 22. The components of the ejector system can be made from any suitable material and are made from metal in the embodiment shown. As shown in FIG. 4, the stack of cutting means rests on plate 25 against which coil springs 24' urge thereby pressing the stack against the inner surface of longitudinally extending flange portions 15 and 16. Upper wall 11 has a notch which permits access to the upper blades in case of jamming.

Operation of the embodiment shown in FIGS. 2-4 will now be described. As the operator pushes block 41 forward, ejector 29 engages the edge of the uppermost cutting means 23 pushing it forward. Since the right edge of side wall 12 has ejector aligning surface 7, the operator is provided greater assurance that the ejector will make contact with the cutting means edge. The height of the upstream access opening allows only the uppermost cutting means to be engaged by ejector 29. As the operator continues to push block 41 forward the uppermost cutting means emerges from the exit slot 20 and begins to seat in cutting means holder 33. When the forward stroke of ejector 29 is completed, the cutting means is firmly seated in its holder. Forward motion of ejector 29 is limited by block 41 striking stop 42. If a used cutting means were in the cutting means holder 33 prior to initiation of the feed operation, the new cutting means would force the used one out of the cutting means holder.

In an automatic sterile docking device the end of the forward motion of block 41 can be detected by a switch to indicate that a fresh cutting means is in place. If the magazine were empty, plate 25 in the magazine mechanically blocks the ejector so that its forward stroke cannot be completed. After a fresh cutting means has been successfully fed to the cutting means holder 33, the operator retracts the ejector thereby permitting the next cutting means in the magazine to be urged into position for the next feed cycle.

I claim:

1. A cutting means magazine for use in an apparatus for forming a connection between two thermoplastic tubes comprising a casing, a stack of disposable cutting means therein, and spring means urging the stack against a wall of the casing; said casing having an exit slot for ejection of the uppermost cutting means of the stack and a cutting means ejector slot for accommodating an ejector, said slot being centrally located in the wall against which the stack is urged and having an upstream access opening to the cutting means and a downstream cutting means access opening which has the exit slot as part thereof; the upstream access opening (a) having an ejector aligning surface with a rise of at least about 0.25 mm and a slope of up to 45° and (b) being from about 50% to about 100% of the cutting means thickness; the downstream access opening being from about 10% to about 80% greater than the cutting means thickness.

2. A magazine according to claim 1 wherein the casing bears opposing projections for holding the magazine temporarily fixedly in the apparatus for forming a connection.

3. A magazine according to claim 2 wherein a plate is situated between the lowermost cutting means and the spring means.

4. A magazine according to claim 3 wherein the spring means consists of two spaced-apart coil springs.

5. A cutting means magazine for use in an apparatus for forming a sterile connection between two internally sterile thermoplastic tubes comprising a generally rectangular housing having a lower wall, an upper wall, a pair of side walls, a rear wall extending between said side walls, a pair of longitudinally extending flange portions, one extending inwardly from the upper wall and the other extending inwardly from the bottom wall, inner edges of said flange portions being spaced to define an ejector slot extending more than from side wall to side wall; said flange portions having inner surfaces which define with one side wall an upstream access opening to the cutting means and with the other side wall a downstream cutting means access opening and exit slot; the sidewall forming the upstream access opening (a) having an ejector aligning surface with a rise of at least about 0.25 mm and a slope of up to 45° and (b) terminating so as to make the access opening about 50% to about 100% of the cutting means thickness; the downstream access opening being from about 10% to about 80% greater than the cutting means thickness;

a stack of disposable cutting means located within said housing and extending about from side wall to side wall; and spring means urging the stack against the inner surface of the longitudinally extending flange portions.

6. A cutting means magazine for use in an apparatus for forming a sterile connection between two internally sterile thermoplastic tubes comprising a generally rectangular housing having a lower wall, an upper wall, a pair of side walls, a rear wall, extending between said side walls, a pair of longitudinally extending flange portions, one extending inwardly from the upper wall and the other extending inwardly from the bottom wall, inner edges of said flange portions being spaced to define an ejector slot extending more than from side wall to side wall; said flange portions having inner surfaces which define with one side wall an upstream access opening to the cutting means and with the other side wall a downstream cutting means access opening and exit slot; the sidewall forming the upstream access opening (a) having an ejector aligning surface with a rise of at least about 0.25 mm and a slope of up to 45° and (b) terminating so as to make the access opening about 50% to about 100% of the cutting means thickness; the downstream access opening being from about 10% to about 80% greater than the cutting means thickness;

a stack of disposable cutting means located within said housing and extending about from side wall to side wall;

spring means urging the stack against the inner surface of the longitudinally extending flange portions; and, intermediate of each side wall, a projection for holding the magazine temporarily fixed in the apparatus for sterile connections.

7. A magazine according to claim 6 wherein a plate is situated between the lowermost cutting means and the spring means.

8. A magazine according to claim 7 wherein the spring means consist of two spaced-apart coil springs.

9. A magazine according to claim 8 wherein the upper wall has intermediate thereof a notch which extends through its longitudinally extending flange portion.

10. A magazine according to claim 9 wherein the slope of the ejector means aligning surface is up to 30°.

11. A magazine according to claim 10 wherein the downstream access opening has a centrally located recess in its bottom surface to provide additional clearance for an ejector and a lip extending from the outer surface of the downstream side wall thereby extending the exit slot.

12. A magazine according to claim 11 wherein the upstream access opening is about 75% to about 100% of the cutting means thickness.

13. In an apparatus for forming a sterile connection between two thermoplastic tubes comprising a disposable cutting means, a pair of mounting blocks adapted to receive and hold two tubes, means to provide movement between said blocks and said cutting means to a position such that the cutting means is between said blocks and traversing where the blocks are adapted to receive tubes, means adapted to realign said blocks to a position where two different tube ends are aligned with and facing each other, and means to separate said blocks and said cutting means while urging said blocks together; the improvement consisting of a magazine according to claim 12 positioned to place a disposable cutting means in a cutting means holder and an ejector slidably mounted for reciprocating movement longitudinally through the ejector slot thereby engaging the near edge of the uppermost cutting means in the magazine; said ejector having an engagement end portion which extends slightly out from the remaining ejector surface adjacent the uppermost cutting means.

* * * * *